United States Patent
Selzer et al.

[11] Patent Number: 5,971,757
[45] Date of Patent: Oct. 26, 1999

[54] IN-LINE FILTER SYSTEM FOR DENTAL INSTRUMENTS

[76] Inventors: Alan Selzer, 707 Larchmont Rd., Elmira, N.Y. 14901; Mark Friedman, 133 Holden Rd., Pine City, N.Y. 14871

[21] Appl. No.: 08/924,565

[22] Filed: Sep. 5, 1997

[51] Int. Cl.[6] .................................................. A61G 5/02
[52] U.S. Cl. ............................................. 433/80; 433/126
[58] Field of Search ................................. 433/80, 81, 82, 433/83, 84, 85, 86, 87, 88, 89, 114, 126

[56] References Cited

U.S. PATENT DOCUMENTS

| | | | |
|---|---|---|---|
| 4,950,159 | 8/1990 | Hansen | 433/80 |
| 4,978,297 | 12/1990 | Vlock | 433/126 |
| 5,204,004 | 4/1993 | Johnston et al. | 433/80 |
| 5,234,338 | 8/1993 | Young | 433/80 |
| 5,252,064 | 10/1993 | Baum et al. | 433/80 |
| 5,474,451 | 12/1995 | Dalrymple et al. | 433/80 |
| 5,554,025 | 9/1996 | Kinsel | 433/80 |
| 5,556,279 | 9/1996 | Wolf et al. | 433/80 |
| 5,709,545 | 1/1998 | Johnson et al. | 433/80 |
| 5,749,726 | 5/1998 | Kinsel | 433/126 |

*Primary Examiner*—Nicholas D. Lucchesi
*Attorney, Agent, or Firm*—Brown, Pinnisi & Michaels, P.C.

[57] ABSTRACT

A filter unit that minimizes the exposure of patients to pathogens found in the dental unit water supply lines (DUWL) while promoting frequent replacement of DUWL filters by providing a disposable microfiltration filter that is easily replaced at low cost. A disk or membrane type filter is placed in an autoclavable filter unit that attaches to the handle of an existing design dental instrument such that the form and function of the dental instrument are not adversely affected. The filter unit, which fits in-line between the dental instrument and the DUWL, includes two portions that are detachably connected by an annular sleeve. When connected, a recess between the portions forms a recess that holds a microfiltration disk filter for filtering water that flows through the dental instrument before it reaches a patient's mouth. The filter unit is easily sterilized after the disk filter is removed. The filter unit is readily adapted to fit standard dental instruments without adversely increasing the size, shape, or weight of the dental instrument.

10 Claims, 3 Drawing Sheets

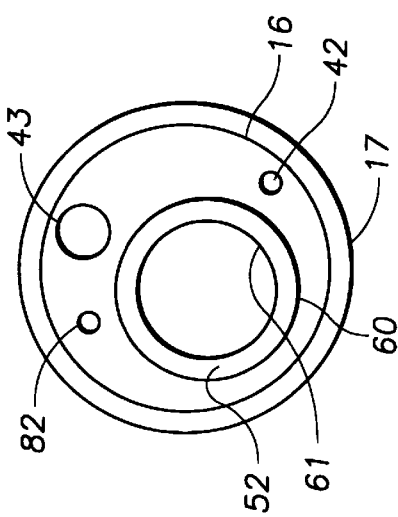
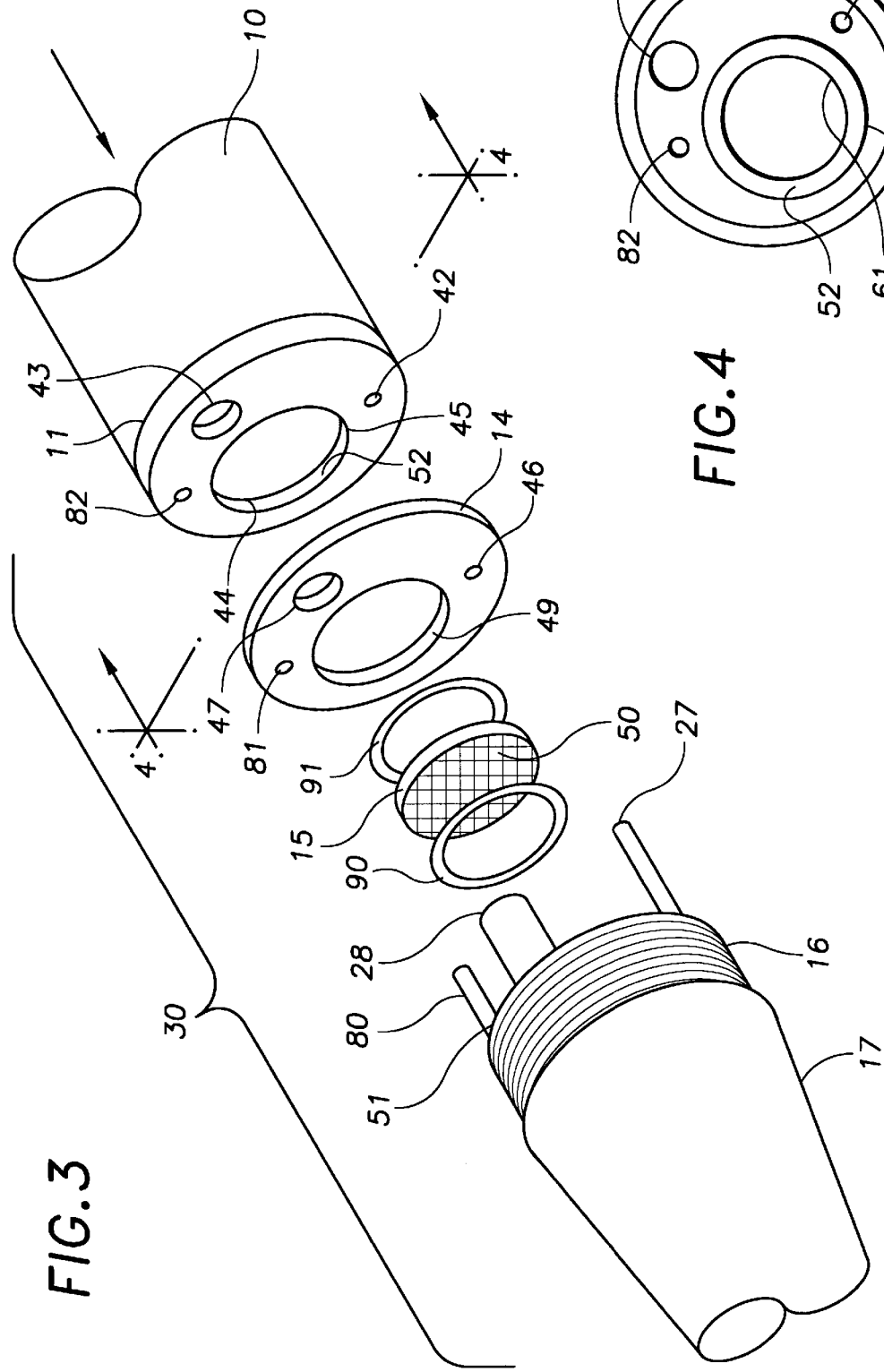

IN-LINE FILTER SYSTEM FOR DENTAL INSTRUMENTS

FIELD OF THE INVENTION

This invention relates to a filter unit for a dental instrument designed for use inside a patient's mouth, and in particular, to an in-line disk filter and filter housing for the type of a dental instrument that delivers water within a patient's mouth.

BACKGROUND OF THE INVENTION

Dentists often use instruments, such as handpieces, ultrasonic scalers, or syringes, that deliver water and air into a patient's mouth during the course of a dental procedure. A pressing concern in the use of such instruments is the risk of infection created by disease-causing microorganisms (pathogens) which build up over the course of time in both the dental unit water line (DUWL) that supplies the instrument and in the tips of the instruments themselves. The DUWL typically extends from the dental instrument to a water source originating either from the municipal water supply or from bottled supplies within the dentist's office. Contamination is particularly promoted within DUWL's because the water in these lines is frequently stagnant since the water flows only when the instrument is in use. There are two principal sources of instrument contamination. The first source of contamination is the pathogens found in the water supply that attach themselves to the walls of the DUWL's. The second source of contamination is the pathogens that are sucked into the instrument and DUWL due to backflow from the patient's mouth (the point of use).

The way in which DUWL's become contaminated is well-known. Basic principles of fluid mechanics dictate that zones of stagnation form around the perimeter of a DUWL. These zones exist because the velocity of flowing water is zero at the walls of the tube. In the absence of agitation, microorganisms breed and flourish in the form of thin biofilms. Found among these organisms are pathogens such as *legionella, pseudomonas*, and *mycobacteria*. Biofilms occasionally break off from the walls of the DUWL and float downstream into a patient's mouth, greatly increasing the risk of infection. Backflow is another significant source of pathogens. Backflow occurs when some of an infected patient's fluids are sucked into the tip of the instrument, eventually contaminating the entire instrument. The risk of pathogen transmission and infection becomes especially significant when immuno-compromised patients, such as HIV-positive victims and cancer victims, are exposed to water from the DUWL.

Conventional methods of sterilization fail to prevent the breeding and growth of pathogens in DUWL's. Simple liquid flushing does not solve the problem, as the biofilms are generally unaffected by flowing liquid. Likewise, flushing with biocide or other decontaminant is ineffective as many organisms are resistant to these chemical treatments. Finally, use of purified water sources to minimize the contaminants in the entering water flow is not a viable solution because pathogens multiply rapidly once the seal on the water supply is opened.

Autoclaving is the most effective method of contaminant control. Although the instrument or instrument head usually is detachable and therefore suitable for autoclaving, the DUWL's generally are not detachable and are too long and unwieldy to be autoclaved. In addition, DUWL's usually are not designed to withstand this sort of treatment.

Several attempts at filtering water flowing via the DUWL through the instrument have proven cumbersome and economically inefficient.

In Hansen, U.S. Pat. No. 4,950,159, a disposable cartridge filter is disclosed which uses activated charcoal in the filter. This material is ill-suited for filtering the water in the DUWL because the pore size of activated charcoal is too large to effectively filter out pathogens.

In Johnston, et. al, U.S. Pat. No. 5,204,004, the filter is not placed in the handle and the DUWL must be cut in order to install a new filter. These limitations are likely to make the instrument cumbersome for a dentist to use and time-consuming to replace. Due to the position of the filter, it does not solve the backflow problem without the use of a separate check-valve or the chemical disinfection of the DUWL between patients, thus adding cost and complexity to its use.

In Dalrymple, et. al, U.S. Pat. No. 5,474,451, a series of air/water filter housings are disclosed. However, the filtering mechanisms entail a multivalent iodine resin/halogen scavenging system. The cost of this scheme precludes frequent replacement and disposal of the filter cartridges. In addition, several of the preferred water treatment embodiments require a filter manifold approximately two inches in length which makes the dental instrument unwieldy. This unwieldiness undercuts the purpose of dental instruments designed for easy manipulation within a patient's mouth. This approach also introduces chemicals into the water which is delivered to the patient's mouth.

In Wolf, et. al, U.S. Pat. No. 5,556,279, the filter is based on a chemical method of decontamination, thus making the filters more expensive and not amenable to frequent disposal. As in Dalrymple, this approach also introduces chemicals into the water which is delivered to the patient's mouth.

Finally, in Kinsel, U.S. Pat. No. 5,554,025, the filter is placed very close to the at the tip of the instrument, in close proximity to the point of use. While this is beneficial for decontamination purposes, it can make the instrument unwieldy due to the location of the filter housing. In addition, the proposed filter design is not suitable for the actual physical orientation of liquid and air tubes in a DUWL. This approach requires the entire filter and housing to be disposed of when changing filters, thus adding to cost. Also, while Kinsel's filter arrangement might be suitable for a dental syringe, it might not be suitable for a handpiece due to the greater volume of water required to cool a handpiece.

The presence and potential harm of pathogens in DUWL's and dental instruments are well-documented and the American Dental Association has called for a solution.

SUMMARY OF THE INVENTION

The present invention provides a filter unit containing a filter that minimizes the exposure of patients to pathogens found in the dental water supply lines while promoting frequent replacement of DUWL filters by providing a disposable microfiltration filter that is easily replaced at low cost. A disk or membrane type filter is placed in an autoclavable filter unit in the handle of an existing design dental instrument such that the form and function of the dental instrument are not adversely affected. The filter unit, which fits in-line between the dental unit and the water line fitting, includes two portions that are detachably connected by an annular sleeve. When connected, a recess between the portions forms a recess that holds a microfiltration disk filter for filtering water that flows through the dental instrument before it reaches a patient's mouth. The filter unit is easily sterilized after the disk filter is removed. The filter unit is readily adapted to fit standard dental instruments without adversely increasing the size, shape, or weight of the dental instrument. The filter unit also prevents backflow from contaminating the dental unit water line. The novel positioning of the filter, the autoclavability of the filter unit, and the disposability of the filter medium between patients also prevent contamination of the DUWL due to backflow.

BRIEF DESCRIPTION OF THE DRAWINGS

FIG. 3 is an exploded perspective view of the filter housing unit, shown in perspective, illustrating a preferred embodiment of a filter and the filter housing unit.

FIG. 4 is a cross-sectional plan view of one portion of the filter housing unit, illustrating a typical configuration of supply and exhaust pipes running through the dental instrument handle.

DESCRIPTION OF THE PREFERRED EMBODIMENT

Figure 1:
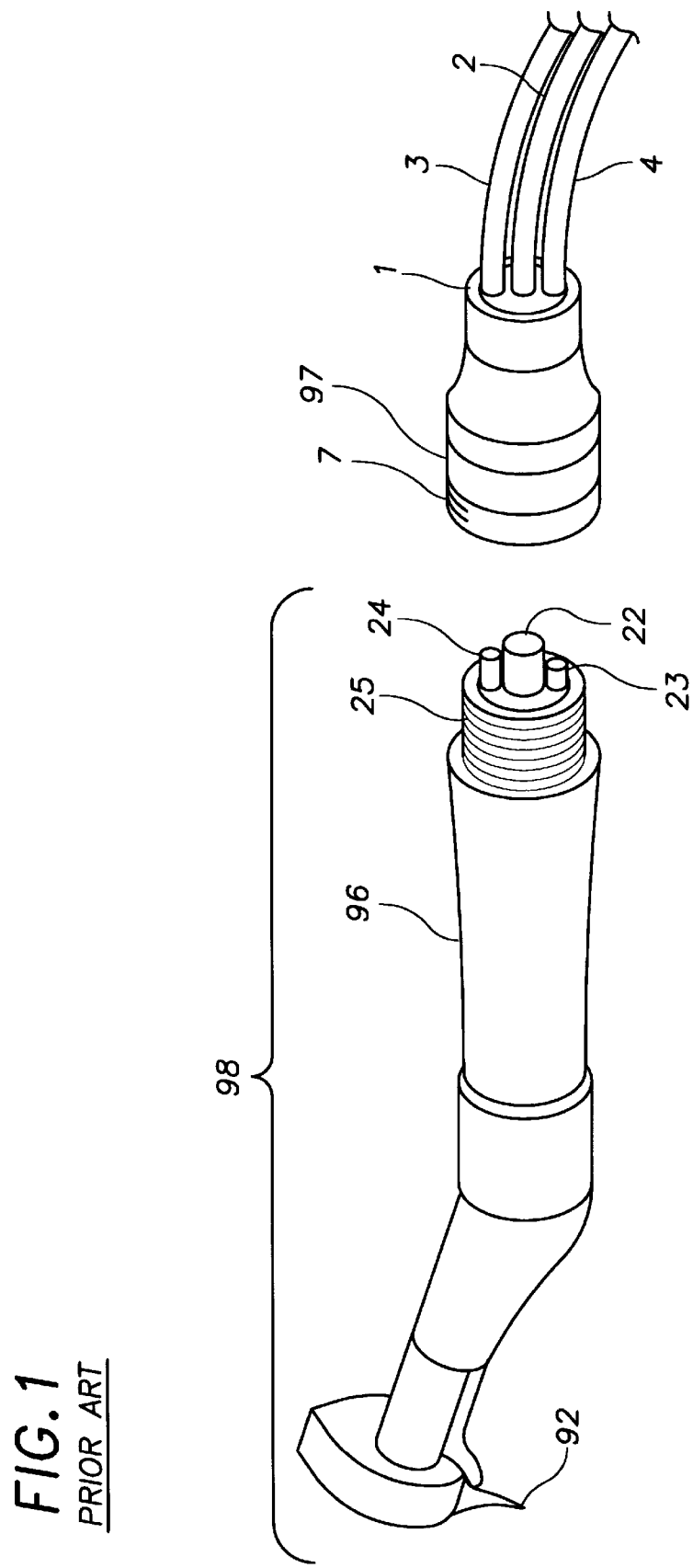
FIG. 1 is a perspective view of a typical prior art dental instrument designed to deliver water and air within a patient's mouth shown with the sections of the handle disconnected.

FIG. 1 shows a dental instrument 98, in this case a dental handpiece, although it will be understood that the invention is equally applicable to syringes or ultrasonic scalers, or any other dental instrument having a water supply. The dental instrument 98 connects to a water line connector 97, which is standardized to allow interconnection of various instruments to the waterline. The connector typically includes a connector insert 1, which connects to the various fluid conduits discussed below, and a threaded or bayonet-equipped sleeve 7, which surrounds the insert 1 and connects it firmly to the mating threads 25 on the instrument handle 96. Water flows in to the instrument through a dental unit water line (DUWL) 2, flowing right to left in FIG. 1.

Water is typically used both to cool tip 92 and to clear debris formed at a point of use (not shown) within a patient's mouth. Other conduits might include a line 3 to supply pressurized air to power the instrument, a conduit 4 to carry air exhaust away, and a conduit to provide air for the aeration of water used within the patient's mouth (shown in FIG. 3). This four-conduit arrangement is currently the most widely used in dentistry. An optical fiber line (not shown) is sometimes provided as well, to supply illumination at the tip of the instrument. All of these are coupled to handpiece fittings such as 22, 23, and 24 through mating sockets in the connector insert 1, and then up through the handle 96 as needed. It will be understood that the number and function of these conduits, the number of fittings on the handpiece, and the matching sockets on the connector insert will vary according to the individual dentist's equipment. So long as there is a water line which requires filtering, adapting the invention to the arrangement of conduits is within the ability of one skilled in the art.

Figure 2:
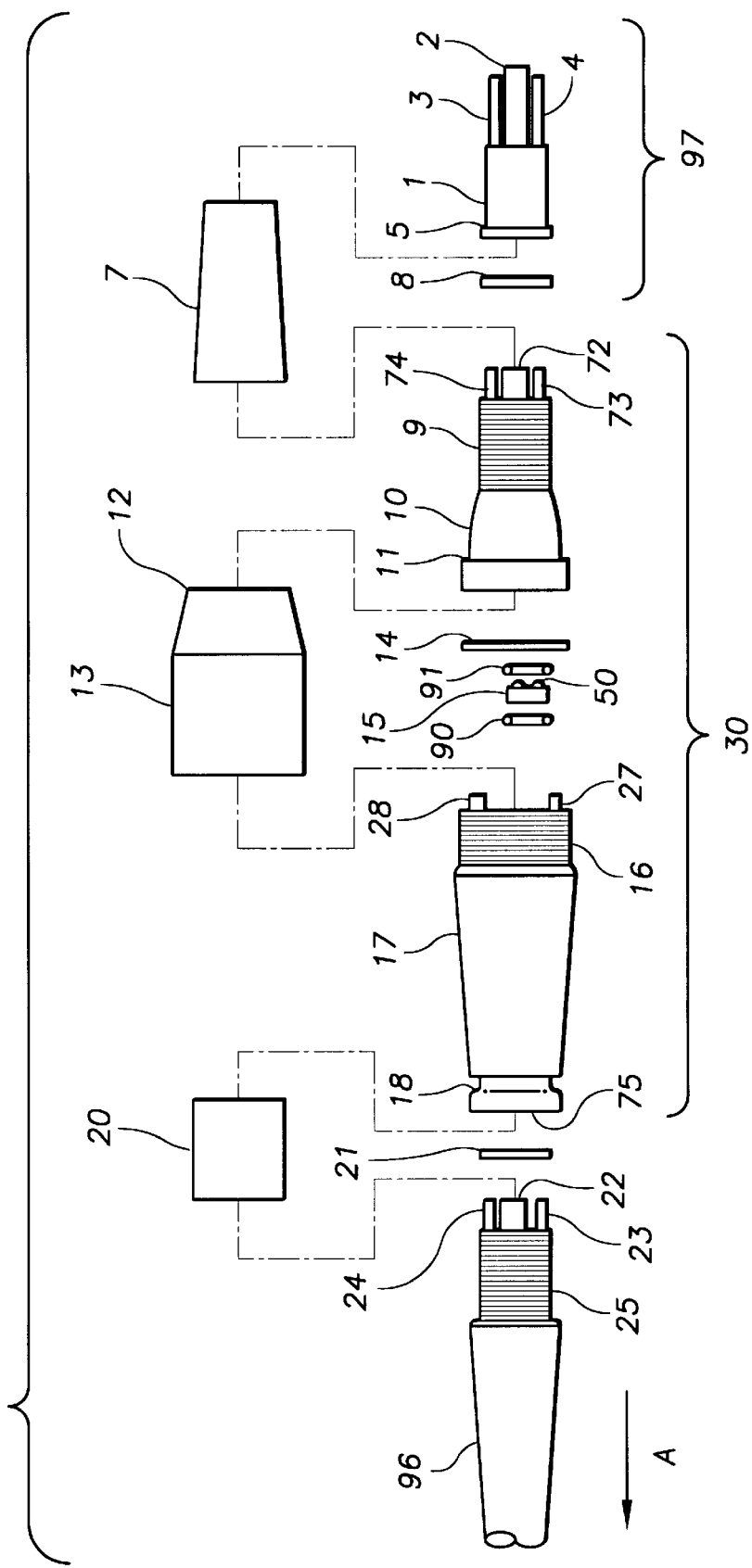
FIG. 2 is an exploded side view of a filter housing unit of the invention.

Referring to FIG. 2, it will be seen that the invention comprises a filter housing unit 30 fitting between the instrument handle 96 and the DUWL connector 97. The housing unit 30 is divided into a first section 17 and a second section 10.

The filter housing unit 30 has, on one end of the second section 10, fittings 72, 73 and 74, which correspond to the fittings 22, 23 and 24 on the dental instrument 90, and thus fit into the mating sockets in the connector insert 1. Threading 9 on the second section 10 of the housing unit interfits with the internal threading on the sleeve 7, which presses up against flange 5, allowing the filter housing 30 to be tightly sealed to the DUWL connector 97. A gasket 8 is used to form a waterproof connection between connector insert 1 and second portion 10 when it is assembled.

The first portion 17 of the filter housing 30 has, on one end, a set of sockets 75 corresponding to those in the connector insert 1, and a sleeve 20, with internal threads corresponding to sleeve 7 on the connector 97, capable of sliding along the first portion 17 until hitting flange 18. This allows the first portion 17 of the filter housing 30 to be connected to the instrument handle 96, with the fittings 22, 23, and 24 fitting into the sockets 75, and the sleeve 20 being threaded onto threads 25 and tightened down against flange 18. As with the other portion, a gasket 21 can be provided between the first portion 17 and the instrument handle 96 to provide a better seal.

The first portion 17 is connected to the second portion 10 of the filter housing unit 30 by means of an annular sleeve 13 with interior threads designed to screw onto matching threads 16 on the first portion 17, drawing in the second portion 10 as constriction 12 pulls in flange 11.

A microfiltration disk filter 15 fits into a recess 52 (shown in FIG. 3) in the end of the second portion 10. A gasket 14 is used to seal the connection formed between the first portion 17 and second portion 10 when assembled with annular sleeve 13. The microfiltration disk 15 is made of autoclavable filter material such as polyethersulfone, and preferably has a pore size of at most 0.22 $\mu$m. Water preferably leaves filter disk 15 with less than 200 colony forming units per milliliter (cfu/mL) at a minimum flow rate of 50 milliliters per minute (mL/min). The filter is preferably disposable and inexpensive, although it could be made of a material which can be sterilized and replaced if desired.

This can be better seen in FIGS. 3 and 4. As can be seen in these figures, the connection face of the first portion 17 is equipped with fluid fittings 27, 28, and 80 for the air inlet line, the air exhaust line, and the water aeration line (and possibly additional fittings, not shown, for optical fiber or other supplies). These fittings mate with sockets 43, 42, and 82 respectively, in the connection face of the second portion 17.

The recess 52 is formed within at least the connection face of one of the portions—here shown as the second portion 10, and is approximately the same diameter as the disk filter 15. If desired, recess 52 may taper from a wider diameter 60 to a narrower diameter 61, so as to center the disk filter 52 within the recess. It will be understood that the recess 52 could also be formed in the end of the first portion 17, or partly in each, within the teachings of the invention.

Preferably, O-rings 90 and 91, and screen 50 (preferably made of metal), serve to hold the filter disk 15 rigid and in place during use. All of these are autoclavable and reusable.

The water inlet line is routed through the connector 97, (see FIG. 2), into fitting 72, then through the second portion 10 to the recess 52. A matching line in the first portion 17, aligned with recess 52, leads the filtered water from the filter 15 through the first portion 17 to the socket 75, and then to fitting 22 in the instrument handle 96. Gasket 14 includes openings 46, 47, 49 and 81 which are tailored to match fittings 27, 28, and 80 as well as an opening for housing disk filter 15.

Gasket 14 is similar in function to gasket 8 and gasket 21 shown in FIG. 2, but can also provide some of the depth required to house the filter, which decreases the required depth of the recess in the connection face of the portions of the filter housing unit.

Thus, filter housing unit 30 (including the gasket 14, and, if used, O-rings 90 and 91 and screen 50) is completely removable from the remainder of the dental instrument. Filter disk 15 is easily replaced, while the component pieces of filter housing unit 30 are easily sterilized in an autoclave. It will also be noted that by this design, the filter housing 30 passes the dental unit water line through the disk filter 15 while allowing the air and other conduits to pass through uninterrupted, without significantly increasing the diameter, length or weight of the dental instrument. The filter is located close to the instrument, without unnecessary tubing between the patient and the filter which could harbor pathogens, and there are no clumsy additional fittings or tubing to get in the dentist's way.

Thus, the present invention minimizes pathogen exposure by preventing pathogens within the DUWL from migrating to the patient's mouth and by permitting sterilization of filter housing unit 30. Those pathogens in locations not subject to sterilization are filtered before reaching the patient's mouth. The water flowing in from the DUWL is filtered and both parts of the filter housing are readily autoclavable. In addition, the invention prevents pathogens from patient's mouth from migrating into the DUWL.

It is understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A filter unit for a dental instrument, said dental instrument having a fluid connector for supply of a fluid to the dental instrument, said connector being adapted to mate with a fluid connector on the fluid supply line, the filter unit comprising:

a body comprising first and second portions having
      a first connector adapted to mate with the connector on the fluid supply line;
      a second connector adapted to mate with the connector of the dental instrument, such that the body attaches to and forms a separable part of the dental instrument;
      a fluid passageway located in the body for conveying fluid from the first connector to the second connector; and
      a chamber for containing a disk filter located in the fluid passageway;
      the first portion of the body having the first connector on one end, a connection face at the opposite end, and the fluid passageway passing from the first connector to the connection face;
      the second portion of the body having the second connector on one end, a connection face at the opposite end, and the fluid passageway passing from the second connector to the connection face;
      the first portion of the body and the second portion of the body being detachably connected to each other at a fluid-tight junction of the connection face of the first portion and the connection face of the second portion; and
   a gasket located between the connection face of the first portion of the body and the connection face of the second portion of the body, the recess being formed at least partially in the gasket; and
   the chamber for containing a disk filter comprises a recess adapted for holding at least part of said disk filter, located between the connection faces of the first and second portions;
      such that fluid from the fluid supply line passes through the connector on the fluid supply line through the first connector into the fluid passageway and through the chamber for containing a disk filter, then through the second connector to the dental instrument without passing through tubing external to the body or the dental instrument after entering the first connector.

2. The filter unit of claim 1, in which the recess is recessed into the connection face of the first portion of the body.

3. The filter unit of claim 1, in which the recess is recessed into the connection face of the second portion of the body.

4. The filter unit of claim 1, in which the recess is recessed partially into the connection face of the first portion of the body and partially into the connection face of the second portion of the body.

5. The filter unit of claim 1, further comprising a disk filter in the chamber, such that the fluid passing through the fluid passageway is filtered by the filter in the container means.

6. The filter unit of claim 5, in which the filter is a microporous disk.

7. The filter unit of claim 6, in which the filter has pores no larger than 0.22 $\mu$m.

8. The filter unit of claim 1, further comprising screen means for supporting the filter, substantially coextensive with the disk filter and fitting within the recess.

9. The filter unit of claim 1, in which the dental instrument has fluid connectors for a plurality of fluids, and the filter unit comprises additional fluid passageways through the body, the additional fluid passageways being separate from the fluid passageway having the container means located therein.

10. The filter unit of claim 9, in which the additional fluid passageways pass axially around the container means for containing a disk filter.

* * * * *

UNITED STATES PATENT AND TRADEMARK OFFICE
CERTIFICATE OF CORRECTION

PATENT NO. : 5,971,757
DATED : October 26, 1999
INVENTOR(S) : Alan Seltzer, et al.

It is certified that error appears in the above-identified patent and that said Letters Patent is hereby corrected as shown below:

On the title page, item [19], change "Selzer et al" to read --Seltzer et al--.

[76] Inventors: Change "Alan Selzer" to read --Alan Seltzer--.

Signed and Sealed this

Sixteenth Day of May, 2000

Attest:

Q. TODD DICKINSON

*Attesting Officer*     *Director of Patents and Trademarks*